United States Patent
Itatani et al.

(10) Patent No.: US 12,252,689 B2
(45) Date of Patent: Mar. 18, 2025

(54) CONVERSION METHOD, CONVERSION AGENT, METHOD FOR PRODUCING ROYAL JELLY COMPOSITION, AND LACTOBACILLUS BACTERIA

(71) Applicant: Yamada Bee Company, Inc., Okayama (JP)

(72) Inventors: Hayate Itatani, Okayama (JP); Ayanori Yamaki, Okayama (JP)

(73) Assignee: YAMADA BEE COMPANY, INC., Okayama (JP)

( * ) Notice: Subject to any disclaimer, the term of this patent is extended or adjusted under 35 U.S.C. 154(b) by 321 days.

(21) Appl. No.: 17/636,724

(22) PCT Filed: Aug. 19, 2020

(86) PCT No.: PCT/JP2020/031319
§ 371 (c)(1),
(2) Date: Feb. 18, 2022

(87) PCT Pub. No.: WO2021/033726
PCT Pub. Date: Feb. 25, 2021

(65) Prior Publication Data
US 2022/0340866 A1 Oct. 27, 2022

(30) Foreign Application Priority Data
Aug. 22, 2019 (JP) ................ 2019-152210

(51) Int. Cl.
*C12N 1/20* (2006.01)
*C12P 7/42* (2006.01)

(52) U.S. Cl.
CPC . *C12N 1/20* (2013.01); *C12P 7/42* (2013.01)

(58) Field of Classification Search
CPC ........ C12N 1/20; C12P 7/42; C12R 2001/225
See application file for complete search history.

(56) References Cited

FOREIGN PATENT DOCUMENTS

| | | |
|---|---|---|
| CN | 101092346 A | 12/2007 |
| CN | 109402182 A | 3/2019 |
| WO | WO 2012/1083477 * | 8/2012 |
| WO | WO-2012108347 A1 * | 8/2012 ............. A23L 21/20 |
| WO | 2016170959 A1 | 10/2016 |
| WO | WO-2017221845 A1 * | 12/2017 ............. A23L 21/20 |

OTHER PUBLICATIONS

WO2017221845A1_Machine Translation Description_ Espacenet, pp. 1-5 (Year: 2017).*
NCBI Blast Search 16S ribosomal RNA, Instant SEQ ID No. 2 vs. AB777202, pp. 1-2 (Year: 2024).*
Arai et al., J. Vet. Med. Sci., 2014, vol. 76, No. 4, pp. 491-498. (Year: 2014).*
WO2017221845A1 Machine Translation Google Patents, pp. 1-6. (Year: 2017).*
"*Lactobacillus* sp. DAT705 gene for 16S ribosomal RNA, partial sequence ", Database GenBank, https://www.ncbi.nlm.nih.gov/nuccore/AB777202, May 1, 2014.
Arai, R., et al., "Development of Duplex PCR Assay for Detection and Differentiation of Typical and Atypical Melissococcus plutonius strains", J. Vet. Med. Sci., 2014, vol. 76, No. 4, p. 491-p. 498.
International Search Report for International Application No. PCT/JP2020/031319; Date of Mailing, Oct. 20, 2020.
Wang, C. et al., "*Lactobacillus panisapium* sp. nov., from honeybee *Apis cerana* bee bread", Int. J. Syst. Evol. Microbiol., 2018, vol. 68, p. 703-p. 708.
PCT International Preliminary Report on Patentability with Written Opinion of the International Searching Authority for International Application No. PCT/JP2020/031319; Date of Mailing, Mar. 3, 2022.
JPO Notice of Reasons for Rejection for corresponding JP Application No. 2021-540969; Issued on Aug. 23, 2022.

* cited by examiner

*Primary Examiner* — Lianko G Garyu
*Assistant Examiner* — Claudia Espinosa
(74) *Attorney, Agent, or Firm* — CANTOR COLBURN LLP

(57) ABSTRACT

Disclosed is a method for converting 10-hydroxy-2-decenoic acid to 10-hydroxydecanoic acid, the method including: reacting *Lactobacillus* bacteria having an ability to convert 10-hydroxy-2-decenoic acid to 10-hydroxy-2-decenoic acid with 10-hydroxy-2-decenoic acid.

2 Claims, No Drawings
Specification includes a Sequence Listing.

SEQUENCE LISTING

<160> NUMBER OF SEQ ID NOS: 2

<210> SEQ ID NO 1
<211> LENGTH: 1493
<212> TYPE: DNA
<213> ORGANISM: Lactobacillus panisapium

<400> SEQUENCE: 1

```
gacgaacgct ggcggcgtgc ctaatacatg caagtcgagc gagcaatttt aacggaatac      60
cttcgggtag gaagataaaa gcgcgagcgg cggatgggtg agtaacacgt gggcaacctg     120 cccctttagct tgggatacca cttggaaaca ggtgctaata ccaaataaga agcaagagcg    180
catgctcaag ctatgaaagg cggctttcga gctgtcacta aaggatgggc ccgcggtgca     240
ttagctagtt ggtaaggtaa cggcttacca aggcaatgat gcatagccga gttgagagac    300
tgatcggcca cattgggact gagacacggc ccaaactcct acgggaggca gcagtaggga    360
atcttccaca atggacgcaa gtctgatgga gcaacgccgc gtgagtgaag aaggttttcg    420
gatcgtaaag ctctgttgtt ggtgaagaag gataaggata gtaactgatt cttatttgac    480
ggtaatcaac cagaaagtca cggctaacta cgtgccagca gccgcggtaa tacgtaggtg    540
gcaagcgttg tccggattta ttgggcgtaa agcgaacgca ggcgggagaa caagtcagct    600
gtgaaagccc tcggcttaac cggggaagtg cagctgaaac tgttttcttt gagtgcagaa    660
gaggagagtg gaactccatg tgtagcggtg gaatgcgtag atatatggaa gaacaccagt    720
ggcgaaggcg gctctctggt ctgtaactga cgctgaggtt cgaaagcatg ggtagcgaac    780
aggattagat accctggtag tccatgccgt aaacgatgag tgctaagtgt tgggaggttt    840
ccgcctctca gtgctgcagc taacgcatta agcactccgc ctggggagta cgaccgcaag    900
gttaaaactc aaaggaattg acgggggccc gcacaagcgg tggagcatgt ggtttaattc    960
gaagcaacgc gaagaacctt accaggtctt gacatctagt gaaaagccta gagataggta   1020 ataccttcg gggacactaa gacaggtggt gcatggctgt cgtcagctcg tgtcgtgaga    1080
tgttgggtta agtcccgcaa cgagcgcaac ccttattatt agttgccagc attaagttgg    1140
gcactctaat gagactgccg gtgacaaacc ggaggaaggt ggggacgacg tcaagtcatc    1200 atgccccta tgacctgggc tacacacgtg ctacaatggt tagtacaacg aggagcaagc    1260
ctgtgaaggc aagcgaatct cttaaagcta atctcagttc ggattgcact ctgcaactcg    1320
agtgcatgaa gctggaatcg ctagtaatcg cggatcagca tgccgcggtg aatacgttcc    1380
cgggccttgt acacaccgcc cgtcacacca tgagagtctg taatacccaa agccggtaag    1440
ataacctgca aaggagtcag ccgtctaagg taggacagat gattagggtg aag           1493
```

<210> SEQ ID NO 2
<211> LENGTH: 1493

```
<212> TYPE: DNA
<213> ORGANISM: Lactobacillus panisapium

<400> SEQUENCE: 2
gacgaacgct ggcggcgtgc ctaatacatg caagtcgagc gagcaatttt aacggaatac      60
cttcgggtag gaagataaaa gcgcgagcgg cggatgggtg agtaacacgt gggcaaccts     120
ccctttagct tgggatacca cttggaaaca ggtgctaata ccaaataaga agcaagagcg     180
catgctcaag ctatgaaagg cggctttcga gctgtcacta aaggatgggc ccgcggtgca     240
ttagctagtt ggtaaggtaa cggcttacca aggcaatgat gcatagccga gttgagagac     300
tgatcggcca cattgggact gagacacggc ccaaactcct acgggaggca gcagtaggga     360
atcttccaca atggacgcaa gtctgatgga gcaacgccgc gtgagtgaag aaggttttcg     420
gatcgtaaag ctctgttgtt ggtgaagaag gatarggata gtaactgatt cttatttgac     480
ggtaatcaac cagaaagtca cggctaacta cgtgccagca gccgcggtaa tacgtaggtg     540
gcaagcgttg tccggattta ttgggcgtaa agcgaacgca ggcgggagaa caagtcagct     600
gtgaaagccc tcggcttaac cggggaagtg cagctgaaac tgttttcctt gagtgcagaa     660
gaggagagtg gaactccatg tgtagcggtg gaatgcgtag atatatggaa gaacaccagt     720
ggcgaaggcg gctctctggt ctgtaactga cgctgaggtt cgaaagcatg ggtagcgaac     780
aggattagat accctggtag tccatgccgt aaacgatgag tgctaagtgt tgggaggttt     840
ccgcctctca gtgctgcagc taacgcatta agcactccgc ctggggagta cgaccgcaag     900
gttaaaactc aaaggaattg acgggggccc gcacaagcgg tggagcatgt ggtttaattc     960
gaagcaacgc gaagaacctt accaggtctt gacatctagt gaaaagccta gagataggta    1020 ataccttcg gggacactaa gacaggtggt gcatggctgt cgtcagctcg tgtcgtgaga    1080
tgttgggtta agtcccgcaa cgagcgcaac ccttattatt agttgccagc attaagttgg    1140
gcactctaat gagactgccg gtgacaaacc ggaggaaggt ggggacgacg tcaagtcatc    1200
atgcccctta tgacctgggc tacacacgtg ctacaatggt tagtacaacg aggagcaagc    1260
ctgtgaaggc aagcgaatct cttaaagcta atctcagttc ggattgcact ctgcaactcg    1320
agtgcatgaa gctggaatcg ctagtaatcg cggatcagca tgccgcggtg aatacgttcc    1380
cgggccttgt acacaccgcc cgtcacacca tgagagtctg taatacccaa agccggtaag    1440
ataacctgca aaggagtcag ccgtctaagg taggacagat gattagggtg aag           1493
```

CONVERSION METHOD, CONVERSION AGENT, METHOD FOR PRODUCING ROYAL JELLY COMPOSITION, AND *LACTOBACILLUS* BACTERIA

CROSS REFERENCE TO RELATED APPLICATIONS

This application is the U.S. National Stage of PCT/JP2020/031319, filed on Aug. 19, 2020, which claims priority under 35 U.S.C. § 119 (a) and 35 U.S.C. § 365 (b) to Japanese patent Application No. 2019-152210, filed on Aug. 22, 2019, the content of which is incorporated by reference herein in its entirety.

TECHNICAL FIELD

The present invention relates to a conversion method, a conversion agent, a method for producing a royal jelly composition, and *Lactobacillus* bacteria.

BACKGROUND ART

10-Hydroxy-2-decenoic acid and 10-hydroxydecanoic acid are components contained in natural royal jelly.

CITATION LIST

Patent Literature

[Patent Literature 1] International Application No. WO2016/170959

SUMMARY OF INVENTION

Technical Problem

It has been confirmed that some physiological activities imparted by components contained in royal jelly, are increased with 10-hydroxydecanoic acid than in 10-hydroxy-2-decenoic acid (for example, Patent Literature 1). The presence of 10-hydroxy-2-decenoic acid sometimes inhibits physiological activities imparted by 10-hydroxydecanoic acid.

One aspect of the present invention is to provide a method and a conversion agent capable of converting 10-hydroxy-2-decenoic acid to 10-hydroxydecanoic acid. In addition, another aspect of the present invention is to provide a royal jelly composition having a high 10-hydroxydecanoic acid content. Furthermore, still another aspect of the present invention is to provide *Lactobacillus* bacteria capable of converting 10-hydroxy-2-decenoic acid to 10-hydroxydecanoic acid with high efficiency.

Solution to Problem

One aspect of the present invention is to provide a method for converting 10-hydroxy-2-decenoic acid to 10-hydroxydecanoic acid, the method including: reacting *Lactobacillus* bacteria having an ability to convert 10-hydroxy-2-decenoic acid to 10-hydroxydecanoic acid with 10-hydroxy-2-decenoic acid.

In the above-described production method, it is preferable that the *Lactobacillus* bacteria be *Lactobacillus plantarum* or bacteria having a 16s rDNA nucleotide sequence showing a homology rate of 95% or more with respect to a nucleotide sequence set forth as SEQ ID NO: 1 or 2.

Another aspect of the present invention is to provide a method for producing a royal jelly composition, including: reacting *Lactobacillus* bacteria having an ability to convert 10-hydroxy-2-decenoic acid to 10-hydroxydecanoic acid with 10-hydroxy-2-decenoic acid in royal jelly.

In the above-described production method, it is preferable that the *Lactobacillus* bacteria be *Lactobacillus plantarum* or bacteria having a 16s rDNA nucleotide sequence showing a homology rate of 95% or more with respect to a nucleotide sequence set forth as SEQ ID NO: 1

Still another aspect of the present invention is to provide a conversion agent for converting 10-hydroxy-2-decenoic acid to 10-hydroxydecanoic acid, the conversion agent including: *Lactobacillus* bacteria having an ability to convert 10-hydroxy-2-decenoic acid to 10-hydroxydecanoic acid.

In the above-described conversion agent, it is preferable that the *Lactobacillus* bacteria be *Lactobacillus plantarum* or bacteria having a 16s rDNA nucleotide sequence showing a homology rate of 95% or more with respect to a nucleotide sequence set forth as SEQ ID NO: 1 or 2.

Still another aspect of the present invention is to provide *Lactobacillus* bacteria having a 16s rDNA nucleotide sequence showing a homology rate of 99% or more with respect to a nucleotide sequence set forth as SEQ ID NO: 1 or 2.

The above-described *Lactobacillus* bacteria may have an ability to convert 10-hydroxy-2-decenoic acid to 10-hydroxydecanoic acid.

Advantageous Effects of Invention

According to one aspect of the present invention, it is possible to provide a method and a conversion agent capable of converting 10-hydroxy-2-decenoic acid to 10-hydroxydecanoic acid. In addition, according to another aspect of the present invention, it is possible to provide a royal jelly composition having a high 10-hydroxydecanoic acid content. According to still another aspect of the present invention, it is possible to provide *Lactobacillus* bacteria capable of converting 10-hydroxy-2-decenoic acid to 10-hydroxydecanoic acid with high efficiency.

DESCRIPTION OF EMBODIMENTS

Hereinafter, an embodiment of the present invention will be described in detail. However, the present invention is not limited to the following embodiments. In the present specification, 10-hydroxy-2-decenoic acid refers to trans-10-hydroxy-2-decenoic acid and is also written as "10-HDA". In the present specification, 10-hydroxydecanoic acid is also written as "10HDAA".

[Conversion Method]

One aspect of the present invention relates to a method for converting 10-HDA to 10HDAA (hereinafter, also simply referred to as a "conversion method"). The conversion method includes reacting *Lactobacillus* bacteria having an ability to convert 10-HDA to 10HDAA with 10-HDA. By reacting the *Lactobacillus* bacteria with 10-HDA, at least a part of 10-HDA can be converted to 10HDAA. Accordingly, the conversion method according to the present embodiment can also be said to be a method for producing 10HDAA by reacting the *Lactobacillus* bacteria with 10-HDA.

(*Lactobacillus* Bacteria)

*Lactobacillus* bacteria used in the conversion method according to the present embodiment can be any *Lactobacillus* bacteria having an ability to convert 10-HDA to 10HDAA. The *Lactobacillus* bacteria preferably can be cultured under both aerobic and anaerobic conditions. The *Lactobacillus* bacteria preferably show an ability to assimilate one or more sugars selected from the group consisting of glucose, maltose, fructose, sucrose, cellobiose, and lactulose and more preferably show an ability to assimilate glucose, maltose, fructose, sucrose, cellobiose, and lactulose.

*Lactobacillus* bacteria having an ability to convert 10-HDA to 10HDAA can be obtained by, for example, isolating *Lactobacillus* bacteria collected from various environments, culturing the bacteria in a medium containing 10-HDA, evaluating an ability to convert 10-HDA to 10HDAA, and selecting those having the conversion ability.

The ability to convert 10-HDA to 10HDAA can be evaluated by, for example, culturing bacteria in a medium containing 10-HDA. Specifically, for example, the evaluation can be performed through the following method. A sample is added to a medium containing 10-HDA and cultured under appropriate conditions (for example, 30° C. to 37° C., MRS medium) in an incubator. A supernatant of the obtained culture liquid is collected. The concentration of 10-HDA and 10HDAA contained in the culture supernatant is measured through high-performance liquid chromatography. The conversion ability is evaluated based on the concentration of 10-HDA and 10HDAA before and after the culture.

The amount of 10HDAA detected in a culture liquid after culturing the *Lactobacillus* bacteria used in the conversion method according to the present embodiment at 35° C. for 120 hours using an MRS liquid medium (pH 6.5) to which 10-HDA is added so that the concentration of 10-HDA becomes about 0.18%, may be 5 mass % or greater of the amount of 10-HDA added before the culture, and is preferably 10 mass % or greater thereof, 20 mass % or greater thereof, 30 mass % or greater thereof, 40 mass % or greater thereof, 50 mass % or greater thereof, 60 mass % or greater, 70 mass % or greater thereof, 80 mass % or greater thereof, 90 mass % or greater thereof, 95 mass % or greater thereof, 97 mass % or greater thereof, 98 mass % or greater thereof, or 99 mass % or greater thereof.

Identification of bacteria isolated from a sample collected through the above-described method, analysis of properties, and the like can be performed through various well-known identification test methods or using commercially available identification kits. In addition, bacteria can be identified through analysis of the 16s rDNA nucleotide sequence, homology searching, and the like.

The *Lactobacillus* bacteria used in the conversion method according to the present embodiment preferably have a 16s rDNA nucleotide sequence showing a homology rate of 95% or more with respect to a nucleotide sequence set forth as SEQ ID NO: 1 or 2. Such *Lactobacillus* bacteria are preferable because they have high ability to convert 10-HDA to 10HDAA. The homology rate of the 16s rDNA nucleotide sequence of *Lactobacillus* bacteria with respect to a nucleotide sequence set forth as SEQ ID NO: 1 or 2 may be 95% or more and is preferably 96% or more, 97% or more, 98% or more, 99% or more, 99.5% or more, and 99.9% or more. The homology rate may be 100%.

The *Lactobacillus* bacteria used in the conversion method according to the present embodiment may be, for example, *Lactobacillus panisapium*. As *Lactobacillus panisapium*, QB3-1-4, QB3-1-9, QB3-1-10, or QB3-2-4 (these four strains are also collectively called a "*Lactobacillus panisapium* M2 strain") or QB9-1-6 (also referred to as a "*Lactobacillus panisapium* M1 strain") shown in examples to be described below is preferable. Such bacterial strains are preferable because they have significantly high ability to convert 10-HDA to 10HDAA.

*Lactobacillus panisapium* M1 strains are available from and deposited on Jan. 16, 2020 in the National Institute of Technology and Evaluation, Patent Microorganisms Depositary Center (NPMD) (Room 122, 2-5-8 Kazusa-kamatari, Kisarazu-shi, Chiba 292-0818) as the Accession Number NITE BP-03106.

An average nucleotide identity (ANI) value of the *Lactobacillus* bacteria used in the conversion method according to the present embodiment with respect to *Lactobacillus panisapium* M1 strains may be 98.3% or more, 98.5% or more, 99% or more, and 99.5%. or more The ANI value can be calculated through ANI analysis using an ANI calculator (http://enve-omics.ce.gatech.edu/ani/index).

The *Lactobacillus* bacteria used in the conversion method according to the present embodiment may be, for example, *Lactobacillus plantarum*. *Lactobacillus plantarum* may be, for example, *Lactobacillus plantarum* b240 (FERM BP-10065).

Substrate

As a substrate in the conversion method according to the present embodiment, synthesized or isolated 10-HDA may be used alone, or a 10-HDA-containing composition may be used. The 10-HDA-containing composition may be, for example, royal jelly.

The royal jelly as a substrate in the conversion method according to the present embodiment may be, for example, raw royal jelly or may be treated royal jelly obtained by treating raw royal jelly. Raw royal jelly can be obtained for example, as a beekeeping product by conventional methods.

Examples of treated royal jelly include: royal jelly concentrates or dilutions prepared by concentrating or diluting raw royal jelly; royal jelly powder prepared by drying and powdering raw royal jelly; enzymatically decomposed royal jelly prepared by treating raw royal jelly with a protease; and royal jelly organic solvent extracts such as royal jelly ethanol extracts prepared by extracting raw royal jelly with an organic solvent such as ethanol. The treated royal jelly may be royal jelly having been subjected to a plurality of treatments. Royal jelly is preferably enzymatically decomposed royal jelly powder which has been enzymatically decomposed and powdered. When enzymatically decomposed royal jelly powder is used, a higher physiological activity can be prepared and allergenicity is reduced, which is preferable.

Royal jelly concentrates can be obtained by, for example, removing moisture content r from raw royal jelly. Royal jelly dilutions can be obtained by, for example, adding water to raw royal jelly.

Royal jelly powder can be obtained by, for example, powdering raw royal jelly through a method well known in this technical field such as freeze-drying, spray-drying, and the like. In addition, royal jelly powder may be obtained through pulverization using a pulverizer (for example, a pin mill, a hammer mill, a ball mill, and a jet mill) after freeze-drying or spray-drying.

Enzymatically decomposed royal jelly can be obtained by, for example, treating raw royal jelly with protease. Examples of protease include enzymes having an endopeptidase action, enzymes having an exopeptidase action, and enzymes having both an endopeptidase action and an exopeptidase action. The protease may be enzymes having at least one of an endopeptidase action and an exopeptidase action, and enzymes having at least an endopeptidase action are preferable and enzymes having both an endopeptidase action and an exopeptidase action are more preferable. Here, the endopeptidase action is an action of decomposing a peptide bond of non-terminal amino acids, and the exopeptidase action is an action of decomposing a peptide bond of terminal amino acids.

Protease includes enzymes having only an exopeptidase action, enzymes having only an endopeptidase action, and enzymes having both an endopeptidase action and an exopeptidase action. Enzymes having both an endopeptidase action and an exopeptidase action are defined as "enzymes having an endopeptidase action" in a case where an endopeptidase action is stronger, defined as "enzymes having an exopeptidase action" in a case where an exopeptidase action is stronger, and defined as "enzymes having both an endopeptidase action and an exopeptidase action" in a case where the degrees of an exopeptidase action and an endopeptidase action are equivalent or almost equivalent to each other. Being equivalent or almost equivalent means that the ratio (activity ratio) of an endopeptidase action to an exopeptidase action is 0.8 times to 1.2 times.

Examples of enzymes having an endopeptidase action include endopeptidases (for example, trypsin or chymotrypsin) derived from animals, endopeptidases (for example, papain) derived from plants, and endopeptidases derived from microorganisms such as lactic acid bacteria, yeast, mold, *Bacillus subtilis*, or Actinomycetes. More specific examples of enzymes having an endopeptidase action include *Bacillus subtilis*-produced peptidase (trade name: Orientase 22BF, Nucleicin), *Bacillus licheniformis*-produced peptidase (trade name: Alcalase), *Bacillus stearothermophilus*-produced peptidase (trade name: Protease S), *Bacillus amyloliquefaciens*-produced peptidase (trade name: Neutrase), and genus *Bacillus*-produced peptidase (trade name: Protamex®).

Examples of enzymes having an exopeptidase action include carboxypeptidase, aminopeptidase, or exopeptidase derived from microorganisms such as lactic acid bacteria, *Aspergillus* bacteria, or *Rhizopus* bacteria. More specific examples of enzymes having an exopeptidase action include *Aspergillus oryzae*-produced peptidase (trade name: Umamizyme G™, Promod® 192P, Promod™ 194P, Sumizyme™ FLAP), *Aspergillus sojae*-produced peptidase (trade name: Sternzyme B15024), genus *Aspergillus*-produced peptidase (trade name: Kokulase™ P), and *Rhizopus oryzae*-produced peptidase (trade name: Peptidase R).

Examples of enzymes having both an endopeptidase action and an exopeptidase action include pancreatin and pepsin. More specific examples of enzymes having both an endopeptidase action and an exopeptidase action include *Streptomyces griseus*-produced peptidase (trade name: Actinase AS), *Aspergillus oryzae*-produced peptidase (trade name: Protease A, Flavourzyme®, ProteAX), and *Aspergillus melleus*-produced peptidase (trade name: Protease P).

The reaction conditions (such as the amount of protease used, the temperature during a reaction, a pH, and a reaction time) when treating raw royal jelly with a protease may be appropriately set depending on the type of protease to be used and the like. Specific examples of reaction conditions in a case where, for example, Actinase AS (Kaken Pharmaceutical Co., Ltd.) having both an endopeptidase action and an exopeptidase action is used as a protease, include an amount of protease used of 1 g per 100 g of royal jelly, a temperature during a reaction of 45° C. to 55° C., a pH of 8.5 to 9.5, and a reaction time during a reaction of 2 to 4 hours.

Royal jelly organic solvent extracts can be obtained by, for example, extracting raw royal jelly using an organic solvent such as ethanol, methanol, propanol, or acetone as a solvent. The extraction time can be appropriately set depending on the form of raw royal jelly used as a raw material, the type and amount of solvent, the temperature during extraction, stirring conditions, and the like. After extraction, solid contents may be removed through filtering, centrifugation, and the like. In addition, an extracted solution may be used as it is or may be used as a concentrated solution or powder by removing a solvent from the solution. Royal jelly organic solvent extracts are preferably royal jelly ethanol extracts.

Commercially available royal jelly may be used. Specific examples of royal jelly include Royal Jelly FD Powder (Nakahara Co., Ltd.), Royal Jelly Extract SF (Matsuura Yakugyo Co., Ltd.), Deproteinized Royal Jelly Powder F (Maruzen Pharmaceuticals Co., Ltd.), and Deproteinized Royal Jelly Extract (API Co., Ltd.)

By reacting 10-HDA as a substrate with the *Lactobacillus* bacteria, at least a part of 10-HDA can be converted to 10HDAA. The reaction between 10-HDA and *Lactobacillus* bacteria can be performed, for example, by culturing the above-described *Lactobacillus* bacteria when in coexistence with 10-HDA or mixing a medium containing 10-HDA with *Lactobacillus* bacteria produced by being cultured in advance. Specifically, for example, a culture liquid containing 10HDAA produced by being converted from at least a part of 10-HDA by culturing (mainly culturing) precultured *Lactobacillus* bacteria in a 10-HDA-containing medium can be obtained.

Culturing of *Lactobacillus* bacteria can be performed, for example, under general conditions suitable for culturing each of *Lactobacillus* bacteria. The culture temperature may be, for example, 25° C. to 40° C. and is preferably 30° C. to 38° C. The pH of a medium may be, for example 5 to 8 and is preferably 6 to 7. The culture time of the preculture may be, for example, 12 to 60 hours. The culture time of the main culture in a 10-HDA-containing medium may be, for example, 60 to 300 hours, and is preferably 90 to 180 hours and more preferably 100 to 130 hours.

The culture of *Lactobacillus* bacteria may be performed under aerobic conditions or anaerobic conditions. From the viewpoint of more efficiently converting 10-HDA to 10HDAA, the culture is preferably performed under anaerobic conditions.

As media for culturing *Lactobacillus* bacteria, various media usually used for culturing *Lactobacillus* bacteria which contain nutritional components such as a carbon source, a nitrogen source, and inorganic salts can be used. Examples of media suitable for *Lactobacillus* bacteria include an MRS medium. As media for main culture, ones obtained by adding 10-HDA or a 10-HDA-containing composition to those media can be used. In addition, as media for main culture, ones obtained by appropriately diluting a 10-HDA-containing composition such as royal jelly in solvents such as water or a buffer solution may be used.

The concentration of 10-HDA in a 10-HDA-containing medium used for main culture may be, for example, 0.001 to 5 mass %, and is preferably 0.01 to 1 mass % and more preferably 0.05 to 0.2 mass %.

In a case where a royal jelly-containing medium is used as a 10-HDA-containing medium used for main culture, the concentration of royal jelly (solid content) with respect to the total amount of medium may be 0.1 to 20 mass %, and is preferably 0.2 to 10 mass % and more preferably 0.5 to 3.5 mass %. In the case of using a royal jelly-containing medium as a medium for main culture, there is a tendency for 10-HDA to be increasingly more efficiently converted to 10HDAA as the concentration of royal jelly in a medium becomes lower.

10HDAA produced through a reaction between 10-HDA and *Lactobacillus* bacteria can be collected by, for example, separating bacterial cells from a culture liquid, collecting a supernatant, and performing a treatment such as concentration and purification as necessary. A culture liquid containing 10HDAA may be used as it is in products such as foods, cosmetics, pharmaceuticals, and quasi-drugs.

[Method for Producing Royal Jelly Composition]

One aspect of the present embodiment relates to a method for producing a royal jelly composition, including reacting 10-HDA in royal jelly with *Lactobacillus* bacteria having an ability to convert 10-HDA to 10HDAA. The royal jelly composition obtained through the production method has a lower concentration of 10-HDA and a higher concentration of 10HDAA than those of raw royal jelly. Therefore, a royal jelly composition enhanced in various physiologically active effects based on 10HDAA can be obtained through the above-described production method. Such a royal jelly composition is preferable because the intake of royal jelly composition can be reduced when it is ingested with the expectation of physiological activities imparted by 10HDAA.

The method for producing a royal jelly composition according to the present embodiment can be performed using royal jelly as a substrate in the above-described conversion method. Regarding a specific embodiment of royal jelly used as a substrate, the same aspect as that of the royal jelly described in the above-described conversion method can be applied. Royal jelly as a substrate is preferably raw royal jelly or enzymatically decomposed royal jelly.

The royal jelly composition obtained through the method for producing a royal jelly composition according to the present embodiment contains 10HDAA. The obtained royal jelly composition may also contain, for example, royal jelly-derived components such as residual 10-HDA, proteins, carbohydrates, lipids, ash, free amino acids, vitamins, and minerals. In addition, the obtained royal jelly composition may contain components that are not derived from royal jelly, for example, bacterial cells (live or dead bacterial cells) of the above-described *Lactobacillus* bacteria and components derived from a medium used for culture.

The content of 10HDAA in the royal jelly composition obtained through the above-described production method with respect to the total amount of solid contents in the royal jelly composition may be, for example, greater than 1.1 mass %, 1.2 mass % or greater, 1.5 mass % or greater, 2.0 mass % or greater, 2.5 mass % or greater, 3.0 mass % or greater, 3.5 mass % or greater, 4.0 mass % or greater, 4.5 mass % or greater, 5.0 mass % or greater, 5.5 mass % or greater, 6.0 mass % or greater, 6.5 mass % or greater, 7.0 mass % or greater, 8.0 mass % or greater, or 10.0 mass % or greater. The content of 10HDAA with respect to the total amount of solid contents in the royal jelly composition may be, for example, 50 mass % or less, or 10 mass % or less.

The content of 10-HDA in the royal jelly composition obtained through the above-described production method with respect to the total amount of solid contents in the royal jelly composition may be, for example, 7.0 mass % or less, 6.0 mass % or less, 5.0 mass % or less, 4.0 mass % or less, 3.5 mass % or less, 3.0 mass % or less, 2.5 mass % or less, 2.0 mass % or less, 1.5 mass % or less, 1.2 mass % or less, 1.0 mass % or less, 0.8 mass % or less, 0.5 mass % or less, 0.3 mass % or less, 0.2 mass % or less, 0.1 mass % or less, 0.01 mass % or less, or 0.001 mass % or less. The above-described royal jelly composition may contain no 10-HDA, that is, the content of 10-HDA may be 0 mass %.

The royal jelly composition obtained through the above-described production method may be used as it is as a product such as a pharmaceutical, a quasi-drug, a food composition, or a cosmetic or may be used as one component of a product such as a pharmaceutical, a quasi-drug, a food composition, or a cosmetic. A product containing a royal jelly composition can be obtained by, for example, adding the royal jelly composition obtained through the above-described method to an intermediate product in a process of producing the product.

In a case where a royal jelly composition is used as a component of a pharmaceutical, a quasi-drug, or a food composition, the pharmaceutical, the quasi-drug, or the food composition may contain components other than the royal jelly composition, for example, pharmaceutically acceptable components (for example, excipients, binding materials, lubricants, disintegrators, emulsifiers, surfactants, bases, dissolution assistants, and suspending agents) and components acceptable as foods (for example, minerals, vitamins, flavonoids, quinones, polyphenols, amino acids, nucleic acids, essential fatty acids, refreshing agents, binders, sweeteners, disintegrators, lubricants, colorants, flavoring agents, stabilizers, preservatives, sustained release adjusters, surfactants, solubilizers, and moistening agents).

Products containing a royal jelly composition may be in any form such as solids, liquids, or pastes or may be in dosage forms such as tablets (including uncoated tablets, sugar-coated tablets, effervescent tablets, film-coated tablets, chewable tablets, troches), capsules, pills, powder agents (powders), fine granules, granules, liquid agents, suspensions, emulsions, syrups, pastes, and injections (including a case of being prepared as liquids by being blended with distilled water or infusions such as an amino acid infusion or an electrolyte infusion when in use). These various preparations can be prepared by, for example, mixing the royal jelly composition obtained through the above-described production method with other components as necessary to form the above-described dosage forms.

In a case where the royal jelly composition obtained through the above-described method is used as a food composition or a component of the food composition, it is preferable that the food composition be one in which a tertiary function, that is, a physical-condition controlling function of food is emphasized. Examples of products in which the tertiary function of food is emphasized include health foods, foods with functional claims, nutrient function foods, nutritional supplement foods, supplements, and foods for specified health uses.

Examples of food compositions include beverages such as coffee, juice, soft drinks such as tea drinks, dairy drinks, lactic acid bacteria drinks, yoghurt drinks, carbonated drinks, and alcoholic drinks such as sake, Western liquors, fruit liquors, and mead; spreads such as custard cream; pastes such as fruit pastes; Western confectionery such as chocolate, donuts, pies, cream puffs, gum, jelly, candies, cookies, cakes and puddings; Japanese sweets such as daifuku, rice cakes, manju, castella, anmitsu, and yokan; ices such as ice cream, ice candy, and sherbet; cooked foods such as curry, gyudon, zosui, miso soup, soup, meat sauce, pasta, pickles, and jam; and seasonings such as dressings, furikake, flavor enhancers, and soup mix.

In a case where the royal jelly composition is used as a component of cosmetics, the cosmetics may contain, as components other than the royal jelly composition, for example, a whitening agent, a moisturizer, an antioxidant, an oily component, an ultraviolet absorber, a surfactant, a thickener, alcohols, a powder component, a coloring material, an aqueous component, water, and various skin nutrients as necessary.

The cosmetics include all cosmetics applied to sites such as the skin, mucous membranes, body hair, hair, the scalp, nails, teeth, facial skin, and the lips of animals (including humans).

The dosage form of the cosmetics according to the present embodiment may be, for example, a solubilized type, an emulsified type, a powder type, an oil liquid type, a gel type, an ointment type, an aerosol type, a water-oil two-layer type, or a water-oil-powder three-layer type. The above-described cosmetics may be, for example, basic cosmetics such as facial cleansers, skin lotion, milky lotion, cream, gel, essences, serum, packs, masks, mists, and UV preventive cosmetics, makeup cosmetics such as foundation, lipstick, cheek rouge, eye shadow, eyeliner, and mascara, facial cleansers, massage agents, cleansing agents, after-shave lotion, pre-shave lotion, shaving creams, body soap, soap, shampoo, hair conditioner, hair treatments, hairdressing agents, hair tonics, hair mists, hair foam, hair liquids, hair gel, hair sprays, hair growing agents, antiperspirants, bath agents, mouth rinse, oral cavity cosmetics, or toothpaste.

[Conversion Agent]

One aspect of the present invention relates to a conversion agent for converting 10-HDA to 10HDAA (hereinafter, also simply referred to as a "conversion agent"). The conversion agent contains *Lactobacillus* bacteria having an ability to convert 10-hydroxy-2-decenoic acid to 10-hydroxydecanoic acid. The conversion agent according to the present embodiment may contain, in addition to the above-described *Lactobacillus* bacteria, at least some components serving as a medium used when culturing the above-described *Lactobacillus* bacteria.

The conversion agent according to the present embodiment can be used by, for example, being seeded in a medium containing 10-HDA. By seeding the conversion agent according to the present embodiment in the 10-HDA-containing medium and reacting the *Lactobacillus* bacteria with 10-HDA, at least a part of 10-HDA can be converted to 10HDAA, that is, 10HDAA can be produced. In addition, in a case where the conversion agent contains a medium component, the conversion agent can be mixed with 10-HDA or a 10-HDA-containing composition, another medium component can be added thereto as necessary, and the mixture can be cultured to convert 10-HDA to 10HDAA.

Regarding a specific embodiment of *Lactobacillus* bacteria used in the conversion agent according to the present embodiment, the same aspect as that of the *Lactobacillus* bacteria described in the above-described conversion method can be applied. In addition, regarding the medium component contained in the conversion agent according to the present embodiment as necessary and the 10-HDA-containing medium to which the conversion agent is applied, the same aspect as that in the case of the 10-HDA-containing medium in the above-described conversion method can be applied.

EXAMPLES

Hereinafter, the present invention will be described in more detail based on examples. However, the present invention is not limited to the following examples.

The details of media and culture methods used in test examples will be shown below

[Preparation of MRS Plate Medium]

An MRS medium was prepared by dissolving 88 g of MRS and 19.2 g of agar in 1,600 mL of distilled water. The MRS medium was sterilized at 121° C. for 20 minutes using an autoclave and was then kept at 60° C. An MRS plate medium was prepared by adding 20 mL of the sterilized MRS medium to each plate and cooling the medium.

[Preparation of MRS Liquid Medium]

110 g of MRS broth was added to 2,000 mL of distilled water and stirred, and the obtained mixed liquid was sterilized at 121° C. for 20 minutes using an autoclave to obtain an MRS liquid medium.

[Preparation of 10-HDA-Containing MRS Liquid Medium]

110 g of MRS broth was added to 2,000 mL of distilled water and stirred, and the obtained mixed liquid was sterilized at 121° C. for 20 minutes using an autoclave. 4 g of 10-HDA was added to the mixed liquid cooled after the sterilization and mixed therewith, and then, the pH was adjusted to 6.5 to obtain a 10-HDA-containing MRS liquid medium.

[Preparation of Diluted Royal Jelly-Containing Medium]

Raw royal jelly (Yamada Bee Farm) or enzymatically decomposed royal jelly (powder) was added to sterile water so that the solid content became 3% (10-fold dilution) or 0.6% (50-fold dilution), and the mixture was mixed. The pH of the obtained mixed liquid was adjusted to 6.5 to obtain a diluted royal jelly-containing medium. A royal jelly aqueous solution of which the pH was adjusted to 7.8 was reacted at 50° C. for 2 hours with ProteAX (Amano Enzyme Inc.) to be hydrolyzed, and crystalline cellulose and locust bean gum were added, and used as enzymatically decomposed royal jelly.

[Plate Culture]

Glycerol stock containing each of various bacterial strains was scraped off with a platinum loop and seeded in the above-described MRS plate medium. The seeded MRS plate medium was incubated for 96 hours under anaerobic conditions at 35° C. using an anaerobic culture kit (Anaero-Pack™, Mitsubishi Chemical Corporation).

Preculture 6 mL each of the above-described MRS liquid medium was dispensed into each conical tube having a capacity of 10 mL. Single colonies were scraped off with a platinum loop from the MRS plate medium cultured for 96 hours and added to the conical tube. Each bacterial strain placed in each conical tube was incubated under anaerobic conditions or aerobic conditions at 35° C. for 48 hours using AnaeroPack to obtain a preculture.

[Main Culture]

6 mL of the above-described 10-HDA-containing MRS liquid medium or the above-described diluted royal jelly-containing medium was dispensed into each conical tube having a capacity of 10 mL. 60 μL of the above-described preculture was added to the conical tube and incubated under anaerobic conditions or aerobic conditions at 35° C. for 120 hours using AnaeroPack. The main culture was similarly performed using a medium containing no 10-HDA or royal jelly as a control, and it was confirmed that there was no 10HDAA detected after the culture and there was no 10HDAA detected after allowing a 10-HDA-containing medium to which no preculture was added to stand under the above-described conditions.

[Evaluation of Conversion Ability From 10-HDA to 10HDAA]

Each supernatant of the culture liquids obtained through the main culture of the various bacterial strains was collected. The concentration of 10-HDA and 10HDAA contained in each culture supernatant was measured through high-performance liquid chromatography (HPLC). The analysis conditions for HPLC were as follows.

Instrument: Prominence (Shimadzu Corporation)

Column: Sunniest C18 (5 μm, 4.6 mm i. d.×250 mm)

Guard column: Sunniest C18 (5 μm, 4.0 mm i.d.×10 mm)

Column oven: 40° C.

Flow rate: 1 mL/min

Mobile phase: A; TFA/ultrapure water=1/1000, B; acetonitrile

Elution method: 25% B (isocratic elution method)

Injection amount: 10 μL

Detector: 10-HDA→PDA: 215 nm, 10HDAA→ELSD: 30° C.; gas pressure of about 300 Pa; Gain 9

The conversion rate from 10-HDA to 10HDAA was obtained based on the amount of 10-HDA remaining in each culture supernatant obtained through the main culture. The conversion rate from 10-HDA to 10HDAA was calculated according to the following equation.

Conversion rate (%)=(1−(concentration of 10-HDA remaining in supernatant/concentration of 10-HDA contained in substrate at the start of culture))×100%

Test Example 1

The abilities to convert 10-HDA to 10HDAA were examined for *Lactobacillus kunkeei* BPS362 strain (NITE P-01835) and baker's yeast through the above-described method. Culture was performed under the aerobic conditions using a diluted royal jelly-containing medium (10-fold dilution, raw royal jelly) as a medium for main culture. In the case where the *Lactobacillus kunkeei* BPS362 and the baker's yeast were used, there was no 10HDAA in supernatants detected after the culture. It was shown that the *Lactobacillus kunkeei* BPS362 and the baker's yeast had no ability to convert 10-HDA to 10HDAA.

Test Example 2

The abilities to convert 10-HDA to 10HDAA were examined for *Lactobacillus* bacteria shown in Table 1 through the above-described method. Culture was performed under aerobic conditions using the above-described 10-HDA-containing MRS liquid medium as a medium for main culture. The amount of 10-HDA and 10HDAA in supernatants of obtained culture liquids was measured, and one in which the concentration of 10HDAA in a supernatant was below the detection limit was evaluated as having no conversion ability and one in which there was 10HDAA in a supernatant detected was evaluated as having a conversion ability. Regarding one having a conversion ability, the conversion rate was measured through the above-described method. The results are shown in Table 1.

TABLE 1

| Bacterial strain name | Accession number | Conversion ability | Conversion rate (%) |
|---|---|---|---|
| *Lactobacillus kunkeei* BPS402 | FERM BP-11439 | None | — |
| *L. paracasei* K71 strain | FERM BP-11098 | None | — |
| *L. plantarum* b240 | FERM BP-10065 | Present | 20 |
| *L. salivarius* UCC118 | NCIMB 40829 | None | — |
| *L. casei* | NBRC 15883 | None | — |
| *L. brevis* | NBRC 12005 | None | — |
| *L. acidophilus* CL-92 | FERM BP-4981 | None | — |
| *L. paracasei* KW3110 | FERM BP-08634 | None | — |
| *L. acidophilus* L-55 | FERM P-18652 | None | — |
| *L. gasseri* OLL 2716 | FERM BP-6999 | None | — |
| *L. pentosus* SAM2336 | FERM BP-10028 | None | — |

Between the examined *Lactobacillus* bacteria, although *Lactobacillus plantarum* b240 had a large amount of 10-HDA remaining in a culture supernatant, presence of some 10HDAA was confirmed only in the *Lactobacillus plantarum* b240. It was confirmed that the *Lactobacillus plantarum* b240 had a slightly weak conversion ability. The conversion rate imparted by the *Lactobacillus plantarum* b240 was 20%.

Test Example 3

Bacterial groups were collected from the intestines of a worker bee, a bee larva, and an adult queen bee. Conversion ability evaluation was performed for five bacterial strains isolated from the intestines of the worker bee, one bacterial strain isolated from the bee larva, and nine bacterial strains isolated from the intestines of the adult queen bee under anaerobic conditions using the above-described 10-HDA-containing MRS liquid medium.

Between the nine bacterial strains, when five strains (QB3-1-4, QB3-1-9, QB3-1-10, QB3-2-4, and QB9-1-6) isolated from the intestines of the adult queen bee were used, it was confirmed that the concentration of 10-HDA in all culture supernatants was below the detection limit and the concentration of 10HDAA detected was high, and therefore substantially the entire amount of 10-HDA was converted to 10HDAA. That is, the conversion rate was 100%. It was shown that the five bacterial strains had a significantly high conversion ability.

On the other hand, there was no 10HDAA detected in culture supernatants in the five bacterial strains isolated from the intestines of the worker bee, one bacterial strain isolated from the bee larva, and the remaining four bacterial strains isolated from the intestines of the adult queen bee. All of these ten bacterial strains whose ability to convert 10-HDA to 10HDAA was not confirmed were identified as *Bifidobacterium* bacteria through a bacterium identification method using matrix-assisted laser desorption ionization-time of flight mass spectrometry (MALDI-TOF MS). It was suggested that the *Bifidobacterium* bacteria did not have an ability to convert 10-HDA to 10HDAA.

Test Example 4

16s rDNA nucleotide sequence analysis was performed under the conditions shown below, on the above-described five bacterial strains (QB3-1-4, QB3-1-9, QB3-1-10, QB3-2-4, and QB9-1-6) whose high conversion ability was confirmed in Test Example 3.

Culture Conditions

Medium: MRS Broth (Oxoid, GBR)+agar
Culture temperature: 37° C.
Culture time: 48 hours
Anaerobic culture
(16s rDNA Nucleotide Sequence Analysis)
　DNA Extraction: Achromopeptidase (FUJIFILM Wako Pure Chemical Corporation)
　PCR Amplification: Tks Gflex DNA Polymerase (Takara Bio Inc.)
　Cycle sequence: BigDye Terminator v3.1 Cycle Sequencing Kit (Applied Biosystems)
　Primer used: PCR amplification: 9F, 1510R
　Sequence: 9F, 515F, 1099F, 53.6R, 926R, 1510R
　Sequence: ABI PRISM3130xi Genetic Analyzer System (Applied Biosystems)
　Nucleotide sequence determination: ChromasPro2.1 (Technelysium)
　BLAST Homology search: analysis software: ENKI (TechnoSuruga Laboratory, Japan)
　Database: International nucleotide sequence database (DDBJ/ENA(EMBL)/GenBank It was confirmed that four bacterial strains (QB3-1-4, QB3-1-9, QBMar. 1, 2010, and QB3-2-4: M2 strains) out of the five bacterial strains had a nucleotide sequence of SEQ ID NO: 1 and one bacterial strain (QB9-1-6: M1 strain) had a nucleotide sequence of SEQ ID NO: 2. In addition, homology search was performed on these five bacterial strains with respect to the international nucleotide sequence database, and as a result, it was shown that substantially the top 30 nucleotide sequences having high homology rates all belonged to the genus *Lactobacillus* and the above-described five bacterial strains all belonged to the genus *Lactobacillus*.

Test Example 5

The conversion ability evaluation between a case of performing main culture on QB9-1-6 (M1 strain) under anaerobic conditions using the above-described 10-HDA-containing MRS liquid medium or a case of performing main culture on QB9-1-6 (M1 strain) under aerobic conditions therewith was compared with each other. As a result, the conversion rates in both anaerobic culture and aerobic culture were 100%, and the same conversion abilities were confirmed.

Test Example 6: Royal Jelly Test

The conversion ability of QB9-1-6 (M1 strain) whose high conversion ability was confirmed was evaluated under anaerobic conditions using a diluted royal jelly-containing medium containing raw royal jelly or enzymatically decomposed royal jelly. As a result, it was confirmed that, although some residual 10-HDA was detected in a supernatant of the medium containing 10-fold or 50-fold diluted raw royal jelly or enzymatically decomposed royal jelly after culture, the concentration of 10HDAA increased compared to that before the culture. It was confirmed that the conversion ability of the QB9-1-6 strain was exhibited even in the case where royal jelly was used as a substrate. In addition, it was confirmed that the conversion rate from 10-HDA to 10HDAA in the case of 50-fold dilution was higher than that in the case of 10-fold dilution. In addition, the same tendency was shown in the case where raw royal jelly or enzymatically decomposed royal jelly was used. The conversion rate under each condition was measured. The results are shown in Table 2.

TABLE 2

| Medium | Dilution | Aerobic/anaerobic | Conversion rate (%) |
|---|---|---|---|
| Raw royal jelly | 50-fold | Aerobic | 100 |
|  |  | Anaerobic | 90 |
| Enzymatically decomposed royal jelly powder | 10-fold | Aerobic | 20 |
|  | 50-fold |  | 70 |
|  | 10-fold | Anaerobic | 100 |
|  | 50-fold |  | 100 |

The conversion ability of QB9-1-6 (M1 strain) was evaluated under aerobic conditions using a 10-fold or 50-fold diluted royal jelly-containing medium containing enzymatically decomposed royal jelly. As a result, it was confirmed that the higher the dilution magnification, the higher the conversion rate from 10-HDA to 10HDAA. It was shown that the higher the dilution magnification of royal jelly, the higher the conversion efficiency also under aerobic conditions.

Test Example 7

Culture was performed under the same conditions as those in Test Example 4 using the five bacterial strains used therein. The culture was performed under anaerobic conditions at 35° C. for 120 hours using a diluted royal jelly-containing medium containing 10-fold diluted enzymatically decomposed royal jelly powder as a medium. The conversion rates of the bacterial strains are shown in Table 3. It was shown that the conversion rate of the M1 strain was particularly high.

TABLE 3

| Strain | Conversion rate (%) |
|---|---|
| QB3-1-4 | 20 |
| QB3-1-9 | 20 |
| QB3-1-10 | 20 |
| QB3-2-4 | 50 |
| QB9-1-6 (M1 strain) | 100 |

Test Example 8

Analysis of average nucleotide identity (ANI) of the M1 strain and the M2 strains with respect to a type strain (Bb2-3$^T$, GenBank accession number: GCA_002916935) of *Lactobacillus panisapium* from Technos Laboratory was performed. The ANI value (homology value) was calculated using an ANI calculator (http://enve-omics.ce.gatech.edu/ani/index). In a case where the ANI value is greater than or equal to 95%, it is determined to be the same species. The ANI values between the type strain, the M1 strain, and the M2 strains are shown in Table 4. Since ANI values of all of the M1 strain and the M2 strains with respect to the type strain are greater than 95%, it became clear that these are *Lactobacillus panisapium*.

TABLE 4

|  | M2 strains | M1 strain |
|---|---|---|
| M1 strain | 98.66 | — |
| Type strain of *Lactobacillus panisapium* | 98.15 | 98.17 |

The invention claimed is:

1. A method for converting 10-hydroxy-2-decenoic acid to 10-hydroxydecanoic acid, the method comprising:
reacting *Lactobacillus panisapium* M1 strain (NITE BP-03106) with 10-hydroxy-2-decenoic acid, wherein the strain has the ability to convert 10-hydroxy-2-decenoic acid to 10-hydroxydecanoic acid, and wherein the conversion rate is 90% or more under anaerobic conditions.

2. A method for producing a royal jelly composition, the method comprising: reacting *Lactobacillus panisapium* M1 strain (NITE BP-03106) with 10-hydroxy-2-decenoic acid in royal jelly, wherein the strain has the ability to convert 10-hydroxy-2-decenoic acid to 10-hydroxydecanoic acid, and wherein the conversion rate is 90% or more under anaerobic conditions.

* * * * *